US010314862B2

(12) United States Patent
Hung

(10) Patent No.: US 10,314,862 B2
(45) Date of Patent: Jun. 11, 2019

(54) HYPOXIA-CULTURED MESENCHYMAL STEM CELLS FOR TREATING ATHEROSCLEROTIC LESIONS

(71) Applicant: NATIONAL YANG-MING UNIVERSITY, Taipei (TW)

(72) Inventor: Shih-Chieh Hung, Taipei (TW)

(73) Assignee: National Yang-Ming University, Taipei (TW)

( * ) Notice: Subject to any disclaimer, the term of this patent is extended or adjusted under 35 U.S.C. 154(b) by 398 days.

(21) Appl. No.: 14/921,465

(22) Filed: Oct. 23, 2015

(65) Prior Publication Data

US 2016/0113968 A1 Apr. 28, 2016

Related U.S. Application Data

(60) Provisional application No. 62/068,491, filed on Oct. 24, 2014.

(51) Int. Cl.
A61K 35/28 (2015.01)
A61K 9/00 (2006.01)
C12N 5/0775 (2010.01)
C12N 5/071 (2010.01)

(52) U.S. Cl.
CPC ............ A61K 35/28 (2013.01); A61K 9/0019 (2013.01); C12N 5/069 (2013.01); C12N 5/0663 (2013.01); C12N 2500/02 (2013.01); C12N 2502/28 (2013.01)

(58) Field of Classification Search
None
See application file for complete search history.

(56) References Cited

U.S. PATENT DOCUMENTS

2004/0258669 A1* 12/2004 Dzau ................... C12N 5/0663
424/93.21
2004/0258699 A1* 12/2004 Bowdish ............... C07K 16/08
506/9

OTHER PUBLICATIONS

Yew et al., J. Tissue Eng. Regen. Med., 12 pages (2012).*
Chen et al., PLoS ONE 9(4): e96161 (2014).*
Apostolakis et al., Cardiovas. Res. 84: 353-360 (2009).*
Hansson, "Inflammation, Atherosclerosis, and Coronary Artery Disease", The New England Journal of Medicine, 2005, pp. 1685-1695.
Witztum et al., "Role of Oxidized Low Density Lipoprotein in Atherogenesis", Perspectives, Dec. 1991, vol. 88, pp. 1785-1792.
Morawietz et al., "Induction of the OxLDL Receptor LOX-1 by Endothelin-1 in Human Endothelial Cells", Biochemical and Biophysical Research Communications, 2001, vol. 284, pp. 961-965.
Li et al., "Antisense to LOX-1 Inhibits Oxidized LDL-Mediated Upregulation of Monocyte Chemoattractant Protein-1 and Monocyte Adhesion to Human Coronary Artery Endothelial Cells", Circulation, Feb. 1, 2000, pp. 2889-2895.

(Continued)

Primary Examiner — Erin M. Bowers
(74) Attorney, Agent, or Firm — Muncy, Geissler, Olds & Lowe, P.C.

(57) ABSTRACT

A method and a pharmaceutical composition for treating an atherosclerotic lesion are provided, including administering a subject in need thereof a therapeutically effective amount of a composition comprising hypoxia-cultured MSCs obtained by culturing auto- or allo-MSCs under low oxygen conditions.

13 Claims, 6 Drawing Sheets

(56) References Cited

OTHER PUBLICATIONS

Blair et al., "Oxidized Low Density Lipoprotein Displaces Endothelial Nitric-oxide Synthase (eNOS) from Plasmalemmal Caveolae and Impairs eNOS Activation", Nov. 5, 1999, vol. 274, No. 45, pp. 32512-32519.

Vieira et al., "Oxidized LDLs alter the activity of the ubiquitinproteasome pathway: potential role in oxidized LDLinduced apoptosis", Inserm U.466, Mar. 2000, vol. 14, pp. 532-542.

Vallance et al., "The effect of endothelium-derived nitric oxide on ex vivo whole blood platelet aggregation in man", Eur J Clin Pharmacol, 1992, vol. 42, pp. 37-41.

Félétou M. "Endothelium-Dependent Regulation of Vascular Tone", Morgan & Claypool Life Sciences, 2011, 70 pages.

Fulton et al., "Regulation of endotheliumderived nitric oxide production by the protein kinase Akt", Nature, vol. 399, Jun. 10, 1999, pp. 597-601.

Chavakis et al., "Oxidized LDL Inhibits Vascular Endothelial Growth Factor-Induced Endothelial Cell Migration by an Inhibitory Effect on the Akt/Endothelial Nitric Oxide Synthase Pathway", 2001, pp. 2102-2107.

Stangl et al., "The ubiquitin-proteasome pathway and endothelial (dys)function", Cardiovascular Research, 2010, vol. 85, pp. 281-290.

Prockop, "Marrow Stromal Cells as Stem Cells for Nonhematopoietic Tissues", Science, vol. 276, Apr. 4, 1997, pp. 71-74.

Huang et al., "Hypoxicmesenchymal stem cells engraft and ameliorate limb ischaemia in allogeneic recipients", Cardiovascular Research, 2014, vol. 101, pp. 266-276.

Kwak et al., "Paracrine action accounts for marked protection of ischemic heart by Akt-modified mesenchymal stem cells", Nature Medicine, vol. 11, No. 4, Apr. 2005, pp. 367-368.

Kinnaird et al., "Local Delivery of Marrow-Derived Stromal Cells Augments Collateral Perfusion Through Paracrine Mechanisms", Circulation, 2004, vol. 109, pp. 1543-1549.

Lowry et al., "Protein Measurement With the Folin Phenol Reagent", J. Biol. Chem. 1951, vol. 193, pp. 265-275.

Tsai et al., "Hypoxia inhibits senescence and maintains mesenchymal stem cell properties through down-regulation of E2A-p21 by Hif-Twist", Blood, vol. 117, No. 2, Jan. 13, 2011, pp. 459-469.

Yew et al., "Efficient expansion of mesenchymal stem cells from mouse bone marrow under hypoxic conditions", Journal of Tissue Engineering and Regenerative Medicine, 2012, 10 pages.

* cited by examiner

HYPOXIA-CULTURED MESENCHYMAL STEM CELLS FOR TREATING ATHEROSCLEROTIC LESIONS

FIELD OF THE INVENTION

The present invention generally relates to a method for treating an atherosclerotic lesion with a composition of hypoxia-cultured mesenchymal stem cells. Especially, the present invention relates to the use of hypoxia-cultured mesenchymal stem cells in restoring the endothelial function in atherosclerotic lesions by secreting cytokines.

BACKGROUND OF THE INVENTION

Atherosclerosis, a vascular disorder leading to alterations and lesions in the inner walls of the blood vessels, underlies several important complications, such as coronary artery disease, stroke, aortic aneurysm, and peripheral arterial disease (Hansson, Inflammation, atherosclerosis, and coronary artery disease, The New England journal of medicine, 2005, 352:1685-1695). Although its etiology is multifactorial, hypercholesterolemia plays a dominant role. It is generally thought modifications of low-density lipoprotein (LDL) lead to its recognition and uptake by macrophage scavenger receptors, resulting in cholesteryl ester accumulation. Modified forms of LDL, such as oxidized LDL (oxLDL), have been previously linked to atherosclerosis (Witztum et al., Role of oxidized low density lipoprotein in atherogenesis, J Clin Invest, 1991, 88:1785-1792). OxLDL promotes endothelial dysfunction by exerting direct cytotoxicity on endothelial cells (Morawietz et al., Induction of the oxLDL receptor LOX-1 by endothelin-1 in human endothelial cells, Biochem Biophys Res Commun, 2001, 284:961-965) and also by enhancing the production of inflammatory mediators (Li et al., Antisense to LOX-1 inhibits oxidized LDL-mediated upregulation of monocyte chemoattractant protein-1 and monocyte adhesion to human coronary artery endothelial cells, Circulation, 2000, 101: 2889-2895). Moreover, oxLDL inhibits endothelial nitric oxide synthase (eNOS) activity and nitrogen oxide (NO) production, leading to interruption of NO-mediated responses in endothelial cells (Blair et al., Oxidized low density lipoprotein displaces endothelial nitric-oxide synthase (eNOS) from plasmalemmal caveolae and impairs eNOS activation, The Journal of biological chemistry, 1999, 274:32512-32519), which is partly attributed to the downregulation of cellular eNOS via the ubiquitin-proteasome pathway (UPP) (Vieira et al., Oxidized LDLs alter the activity of the ubiquitin-proteasome pathway: potential role in oxidized LDL-induced apoptosis, FASEB journal: official publication of the Federation of American Societies for Experimental Biology, 2000, 14:532-542).

NO plays an important role in maintaining vessel functions, including vascular tone, platelet aggregation, smooth muscular proliferation, and leukocyte adhesion to endothelial cells (Valiance et al., The effect of endothelium-derived nitric oxide on ex vivo whole blood platelet aggregation in man, European journal of clinical pharmacology, 1992, 42:37-41). The preponderant isoform of NOS in healthy endothelial cells is eNOS. The endothelium-dependent vasorelaxation is eNOS-dependent because eNOS$^{-/-}$ mice show elevated systemic and pulmonary arterial pressures and reduced endothelium-dependent relaxations in response to acetylcholine (Félétou, Endothelium-dependent regulation of vascular tone, 2011). For well-controlled normal NO production, eNOS activity is highly regulated by post-translational modifications. Phosphorylation of eNOS at Ser1177 by Akt/protein kinase B (PKB) activates eNOS (Fulton et al., Regulation of endothelium-derived nitric oxide production by the protein kinase Akt, Nature, 1999, 399:597-601), while disruption of its association with Akt by oxLDL deactivates eNOS (Chavakis et al., Oxidized LDL inhibits vascular endothelial growth factor-induced endothelial cell migration by an inhibitory effect on the Akt/endothelial nitric oxide synthase pathway, Circulation, 2001, 103:2102-2107). Besides, eNOS availability regulated by UPP also plays a crucial role in maintaining vessel functions (Stangl et al., The ubiquitin-proteasome pathway and endothelial (dys) function, Cardiovascular research, 2010, 85:281-290), despite few studies in this area.

Mesenchymal stem cells (MSCs), such as Bone marrow-derived MSCs, are capable of self-renewal and have the potential to differentiate into mesenchymal and non-mesenchymal tissues (Prockop, Marrow stromal cells as stem cells for nonhematopoietic tissues, Science, 1997, 276:71-74). MSCs when transplanted in a murine model of hindlimb ischemia revascularize and ameliorate ischemic limb (Huang et al., Hypoxic mesenchymal stem cells engraft and ameliorate limb ischaemia in allogeneic recipients, Cardiovasc Res, 2014, 101:266-276). The effect of MSCs therapy has recently been reported to be affected by a mechanism of endocrine or paracrine effects (Gnecchi et al., Paracrine action accounts for marked protection of ischemic heart by Akt-modified mesenchymal stem cells, Nature medicine, 2005, 11:367-368; Kinnaird et al., Local delivery of marrow-derived stromal cells augments collateral perfusion through paracrine mechanisms, Circulation, 2004, 109: 1543-1549). Successful cases with cell therapy in clinical are still few. For example, transplantation of MSCs is beneficial in treatment of myocardial infarction and hindlimb ischemia.

SUMMARY OF THE INVENTION

This invention is based on the unexpected finding that hypoxia-cultured mesenchymal stem cells (MSCs) are effective in repairing a lesion, particularly atherosclerotic lesion.

Accordingly, the present invention provides a method for treating atherosclerotic lesion, comprising administering a subject in need thereof a therapeutically effective amount of a composition comprising hypoxia-cultured mesenchymal stem cells (MSCs) obtained by culturing auto- or allo-MSCs under low oxygen conditions less than 10% oxygen.

In another aspect, the present invention provides a method for treating atherosclerotic lesion, comprising a therapeutically effective amount of hypoxia-cultured mesenchymal stem cells (MSCs). In some embodiments, the hypoxia-cultured MSCs are obtained by culturing auto- or allo-MSCs under low oxygen conditions less than 10% oxygen.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Figure 1A:
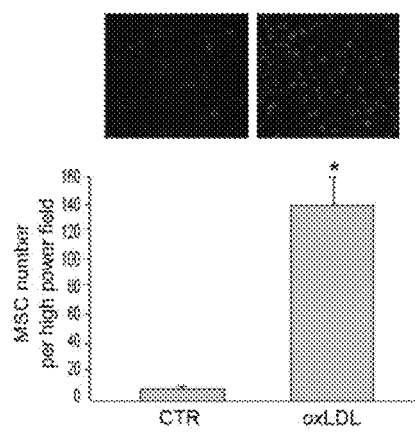
FIGS. 1A-1D show the effect of MSCs on oxLDL-induced HUVEC damage, followed by FIG. 1A (transwell migration assays), which HUVECs were seeded in the lower wells without (CTR) or with oxLDL treatment (50 μg/mL), while MSCs were seeded in the upper wells and assayed at 24$h$. The FIG. 1A (top), which representative views of the fields in transwell membranes, showing the stained MSCs that migrated to the lower membrane side of transwells; the FIG. 1A (bottom), quantification of the number of migrated MSCs per high power field. Data are the average numbers of migratory cells in 8 high-power fields (40×). Each experiment was performed in triplicate *p<0.05 vs CTR. The FIG. 1B shows that HUVECs were treated with indicated concentration of oxLDL for 24 h, followed by quantitative RT-PCR analysis of GAPDH (glyceraldehyde-3-phosphate dehydrogenase). The HUVECs ($1.5 \times 10^4$ cells) were treated without or with 50 μg/mL oxLDL in the absence or presence of indirect coculture with MSCs ($5 \times 10^3$ cells) for 24 h, followed by (FIG. 1C) Western blot analysis and (FIG. 1D) assay of the culture supernatants for determining the NO production by using Griess method (n=6 in each group). *p<0.05 vs. CTR, #p<0.05 vs. CTR or oxLDL.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The present invention, provides a method for treating an atherosclerotic lesion, comprising administering a subject in need thereof a therapeutically effective amount of a composition comprising hypoxia-cultured MSCs.

In one embodiment of the invention, the MSCs are obtained by culturing auto- or allo-MSCs under low oxygen conditions less than 10% oxygen.

As used herein, the term "atherosclerotic lesion," also known as "altherosclerosis," refers to a specific form of arteriosclerosis in which an artery wall thickens as a result of invasion and accumulation of white blood cells. Atherosclerotic lesion or atherosclerosis is therefore a syndrome affecting arterial blood vessels due to a chronic inflammatory response of WBCs in the walls of arteries, which would be found in the subjects suffering from some diseases or disorders associated with arterial blood vessels, such as coronary artery disease, stroke, aortic aneurysm, or peripheral arterial disease. Normally, atherosclerotic lesion includes coronary atherosclerosis, cerebral atherosclerosis, aortic atherosclerosis, or renal artery atherosclerosis.

As used herein, the term "mesenchymal stem cells" or "MSCs" refers to multipotent stem cells, which can differentiate into a variety of cell types, including for example, osteoblasts, chondrocytes and adipocytes etc. The mesenchymal stem cells or MSCs may be derived from any tissue sources, including but not limited to bone marrow tissues, adipose tissue, muscle tissue, corneal stroma or dental pulp of deciduous baby teeth, umbilical cord tissues or umbilical cord blood etc. In one example of the invention, the MSCs are bone marrow MSCs.

The term "hypoxia" used herein refers to a condition of reduced oxygen content of air, such as less than 10% oxygen, preferably 1% to 7% oxygen.

In the present invention, the hypoxia-cultured MSCs are obtained by culturing auto- or allo-MSCs under low oxygen conditions less than 10% oxygen. In one example of the invention, the MSCs are cultured under the oxygen content ranging from 1% to 7% oxygen. The MSCs may be auto- or allo-MSCs. In one example of the invention, the MSCs are allo-MSCs. In one example of the invention, the MSCs are isolated auto- or allo-bone marrow MSCs after culturing under a hypoxic condition with 1% to 7% oxygen for at least 2 passages.

According to the invention, the hypoxia-cultured MSCs are in a composition for administration. For example, the composition may be administered through intravenous injection, intracoronary injection, intracardiac injection, intraperitoneal injection, or local application. In some embodiments of the invention, the composition is applied through parenteral administration.

Schedules and dosages for administration can be determined in accordance with known methods for these products, for example using the manufacturers' instructions. For example, a MSC cell preparation can be supplied at a dose of $2 \times 10^6$ cells/kg of MSCs in either 10 mL or 50 mL single-use vials. An exemplary suitable dosage range for a hypoxia-cultured MSC composition of the invention may between about $5 \times 10^5$ cells/kg and $8 \times 10^6$ cells/kg. Quantities and schedule of injection of hypoxia-cultured MSCs for 24 hours, 48 hours 72 hours or a week or a month once or more can be determined considering the efficiency of the MCS treatment and its pharmacokinetic parameters. However, it will be appreciated that these schedules are exemplary and that optimal schedule and regimen and the tolerability of the antibodies must be determined in clinical trials.

Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For parenteral administration, injection is preferred, including intramuscular, intravenous, intraperitoneal, and subcutaneous. For injection, the compositions of the invention may be formulated in aqueous solutions, preferably in physiologically compatible buffers such as Hanks' solution, Ringer's solution, or physiological saline buffer. In addition, the compounds may be formulated in solid form and redissolved or suspended immediately prior to use. Lyophilized forms are also included.

For oral administration, the compositions can be formulated by combining the active compounds with pharmaceutically acceptable carriers well known in the art. Such carriers enable the compositions of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

The term "therapeutically effective amount" or "effective amount" refers to a predetermined amount calculated to achieve the desired effect, i.e., to prevention or treatment. In certain embodiments of the invention, the pharmaceutical composition comprises $2 \times 10^5$-$8 \times 10^6$ cells/kg of MSCs, preferably $5 \times 10^5$-$8 \times 10^6$ cells/kg of MSCs, more preferably $5 \times 10^5$-$5 \times 10^6$ cells/kg of MSCs, most preferably $8 \times 10^5$-$5 \times 10^6$ cells/kg of MSCs.

The present invention is further illustrated by the following examples, which are provided for the purpose of demonstration rather than limitation.

In the example of the invention, it is evidenced that the levels of phospho-Akt, phospho-endothelial nitric oxide synthase (eNOS), and total eNOS, and enhance nitrogen oxide (NO) production in the subject are increased through the administration of the composition comprising hypoxia-cultured MSCs. Therefore, the endothelium-dependent relaxation and inhibit plaque formation in the subject are increased through the administration of the composition comprising hypoxia-cultured MSCs.

EXAMPLES

The other characteristics and advantages of the present invention will be further illustrated and described in the following examples. The examples described herein are using for illustrations, not for limitations of the invention.

The practice of the present invention will employ technologies comprising conventional techniques of cell biology, cell culture, and genetic engineering, which are within the ordinary skills of the art. Such techniques are explained fully in the literature.

Preparation and Characteristics of Isolated Hypoxia-Cultured MSCs

The preparation and characteristics of isolated hypoxia-cultured MSCs were described in previous studies (Tsai et al., Hypoxia inhibits senescence and maintains mesenchymal stem cell properties through down-regulation of E2A-p21 by HIF-TWIST, Blood, 2011, 117:459-469; Yew et al., Efficient expansion of mesenchymal stem cells from mouse bone marrow under hypoxic conditions, Journal of tissue engineering and regenerative medicine, 2013, 7:984-993). For hypoxic culture, MSCs were cultured in a gas mixture composed of 94% N2, 5% $CO_2$, and 1% $O_2$. Briefly, bone marrow aspirates were taken from the iliac crest of normal adult donors after informed consent and under a protocol approved by an Institutional Review Board. Nucleated cells were isolated by a density gradient (Ficoll-Paque; Pharmacia; Peapack, N.J.) and resuspended in complete culture medium [CCM: α-MEM (α-minimal essential medium; Gibco-BRL, Gaithersburg, Md.) supplemented with 10.0% fetal bovine serum (FBS), 100 units/mL penicillin, 100 μg/mL streptomycin, and 2 mM L-glutamine].

Animals and MSC Transplantation Regimen

The animal study protocol was approved by the Animal Experimental Committee of Taipei Veterans General Hospital. Male, 8-week-old apolipoprotein E-deficient (apoE$^{-/-}$) mice (C57BL/6-KO-apoe$^{tm1Unc}$/J, Jackson Laboratories) were used for this study. The animals were maintained in a 22° C. room with a 12-h light/dark cycle and received drinking water ad libitum. The 58Y1 diet (60% fat & 0.03% cholesterol; Test Diet; PMI Nutrition International, Richmond, Ind.) was chosen to create the atherosclerotic lesions because it elevates blood cholesterol levels similar to that in human atherosclerosis. All experimental mice were fed with 58Y1 for 5 weeks and then received a single-dose of MSCs ($2\times10^5$ cells) by intravenous tail vein injection. Control animals received a corresponding amount of PBS solution without cells. After cell/PBS treatment, all mice were fed with normal chow for 7 days, when tissue samples and blood were collected immediately. Plasma lipid concentrations were determined by routine chemical methods.

OxLDL Preparation

Plasma in the presence of ethylenediaminetetraacetic acid (EDTA) was used to isolate LDL by sequential ultracentrifugation ($1.019 < d < 1.063$ kg/L). Afterward, native LDL was dialyzed at 4° C. for 24 h against 1000 volumes of phosphate-buffered saline (PBS) to remove EDTA. To initiate oxidation, LDL (0.5 g protein/L) was exposed to 5M $CuSO_4$ for 18 h. The generation of thiobarbituric acid-reactive substances was monitored by the fluorometric method, and the values of the malondialdehyde equivalents increased from 0.76±0.21 nmol/mg protein of native LDL to 24.3±2.6 nmol/mg protein of $CuSO_4$-treated LDL. The freshly prepared oxLDL was dialyzed at 4° C. for 48 h against 500 volumes of PBS to remove $Cu_2+$ and was sterilized by passage through a 0.22-μm filter. The protein contents of native LDL and the oxLDL preparations were measured by the Lowry assay (Lowry et al., Protein measurement with the Folin phenol reagent, J Biol Chem, 1951, 193:265-275).

Aortic Ring Preparations and Tension Recording

Sections of the thoracic aorta 2 mm below the subclavian artery were excised carefully and fixed isometrically in organ chambers (7 ml) containing a modified Krebs' solution: 120 mMNaCl, 4.5 mMKCl, 2.5 mM $CaCl_2$, 1 mM $MgSO_4$, 27 mM $NaHCO_3$, 1 mM $KH_2PO_4$, and 10 mM glucose maintained at 37° C. and through which a mixture of 95% $O_2$, 5% $CO_2$ was bubbled. Briefly, aortic rings of 2 mm in length were equilibrated under passive tension for 30 mM. During this time, the tissues were washed every 15 mM. After equilibration, the aortic rings were stabilized with a near maximal contraction induced by phenylephrine ($10^{-6}$ M). After the rings achieved a stable contractile tension, drugs were added in increasing concentrations to obtain cumulative concentration-response curves: $10^{-9}$ M to $10^{-5}$ M phenylephrine, $10^{-9}$M to $10^{-5}$M acetylcholine (assessment of endothelium-dependent aortic ring relaxation after precontraction with phenylephrine), and $10^{-11}$ M to $10^{-5}$ M nitroglycerin (assessment of endothelium-independent aortic ring relaxation after precontraction with phenylephrine). The drug concentration was increased when aortic ring constriction or relaxation was completed. Drugs were washed out before the next substance was added.

Real-Time RT PCR

The mRNA levels were quantified by real-time RT-PCR array on the $RT^2$ Profiler PCR Array of Human Cytokines & Chemokines Array (SABiosciences, Frederick, Md.) according to the manufacturer's instructions. Briefly, total RNA (2 μg) was reverse-transcribed into first-strand cDNA and used as a template to perform real-time PCR on the ABI PRISM 7700 sequence detection system (Applied Biosystem, Foster City, Calif.). The PCR annealing step was at 60° C. for 30 sec. PCR amplification of glyceraldehyde-3-phosphate dehydrogenase and hypoxanthine guanine phosphoribosyl transferase 1 was performed for each sample to control for sample loading and allow for normalization between samples. The data were analyzed using the comparative ΔΔCt method, according to the PCR Array Data Analysis downloaded from the SABiosciences website. Expression of the target gene SDF-1α, IL8, MIP-2 and the endogenous reference GAPDH was quantified using the primers, probes, and standards. The primers and TaqMan probes were designed using the software Primer Express (Applied Biosystem). RT-PCR was performed according to a TaqMan 2-step method using an ABI PRISM 7700 sequence detection system (Applied Biosystem).

Statistical Analysis

All statistical analyses were performed with the SPSS software, version 18.0 (SPSS, Inc, Chicago, Ill.). Overall comparison between two groups was performed with the Student's t test. Comparison between three or more groups was performed with the ANOVA with appropriate post hoc LSD testing between different groups. Quantitative data were presented as means±SEM from at least three independent experiments. The criterion of significance was set as p<0.05.

Example 1. MSCs Restore Akt/eNOS Activation and Stabilize eNOS in oxLDL-Treated Endothelial Cells To examine the tissue repair potential of exogenous MSCs on atherosclerotic lesion, we first examined the recruitment of MSCs by atherosclerotic endothelium in transwell migration assay. Human umbilical vein endothelial cells (HUVECs) were obtained from the Bioresource Collection and Research Center (BCRC, Hsinchu, Taiwan), cultured in ECGM-2 according to the manufacturer's instructions, and used from passage 6 to 8. Cells were maintained at 37° C. under 5% $CO_2$.

Equal aliquots of HUVECs ($5 \times 10^5$) in 600 µl of ECGM2+10% FBS without or with oxLDL (50 µg/ml) were placed in the low chambers of Costar polycarbonate transwells (8 µm pore size; Corning Costar, NY), while $1 \times 10^5$ MSCs in 100 µL of ECGM2+1% FBS were added to the top chambers of the transwells. Cells without oxLDL treatment served as the control. After migration for 24 h, the remaining cells on the upper surface of the membrane were removed by wiping with a cotton swab and migratory cells on the membrane underside were fixed using 5% (wt/vol) glutaraldehyde and stained using 4',6-diamidino-2-phenylindole (DAPI). Filter inserts were inverted and the numbers of DAPI stained cells were determined by fluorescence microscopy. Data were presented as the average number of migratory cells calculated from 8 high-power fields (40×). Each experiment was performed in triplicate, and then the data were averaged for statistical analysis.

Figure 1B:
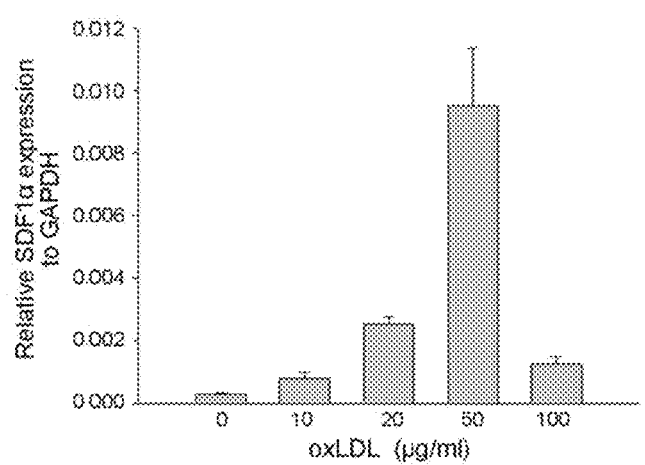

The results of transwell migration assay showed in FIG. 1A demonstrated that oxLDL-treated HUVECs increased in the recruitment of MSCs compared to HUVECs treated with the vehicle. We also demonstrated SDF-1α, the chemokine attracting MSCs, expressed by HUVECs was dose-dependently enhanced by oxLDL treatment with the peak at 50 µg/ml (FIG. 1B), which was the concentration of oxLDL used in the following experiments.

We then examined whether indirect coculture of MSCs protected HUVECs from oxLDL-induced damage. It is well known oxLDL induces endothelium damage through the suppression of phospho-Akt, phospho-eNOS, and total eNOS levels. The HUVECs ($1.5 \times 10^4$ cells) were treated without or with 50 µg/mL oxLDL in the absence or presence of indirect coculture with MSCs ($5 \times 10^3$ cells) for 24 h, followed by Western blot analysis.

Cell extracts were prepared with M-PER (Pierce, Rockford, Ill.) plus protease inhibitor cocktail (Halt; Pierce) and protein concentrations were determined using the BCA assay (Pierce). Equal amounts of cellular proteins were then electrophoresed in an SDS-polyacrylamide gel, and proteins were then transferred to PVDF membranes (Amersham Biosciences Co., Piscataway, N.J.). Nonspecific binding sites on the membranes were blocked with 5% nonfat milk at 4° C. overnight. Membranes were reacted with first Ab. The membranes were then probed with their respective secondary Ab conjugated with horseradish peroxidase. The bands were visualized using an enhanced chemiluminescence kit (Perkin Elmer Life Science, Boston, Mass.) and detected with X-ray film.

Figure 1C:
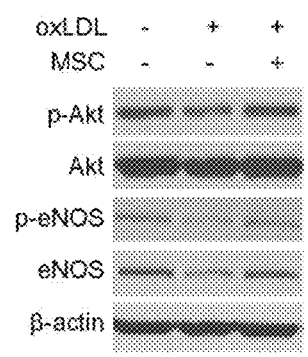

As expected, HUVECs treated with oxLDL decreased in the levels of phospho-Akt, phospho-eNOS, and total eNOS (FIG. 1C). Interestingly, we found indirect coculture with MSCs abrogated oxLDL-induced decrease in the levels of phospho-Akt, phospho-eNOS, and total eNOS (FIG. 1C).

Figure 1D:
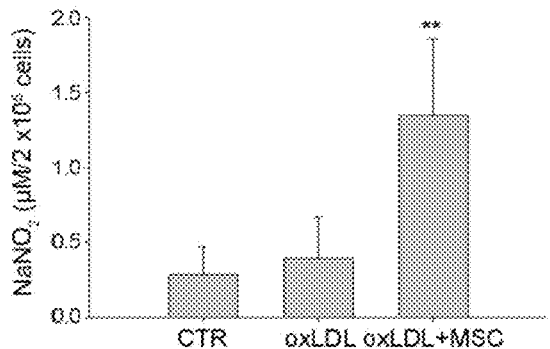

NO levels were measured by the Griess method after conversion of nitrate to nitrite by nitrate reductase by using the commercially available kit (Nitrate/Nitrite colorimetric assay kit, Cayman Chemical Co., cat no: 780001) according to the manufacturer's recommendations. Briefly, 100 µl culture supernatant was reacted with an equal volume of Griess reagent for 10 min at room temperature in the dark. Total nitrite was measured as NO levels at 540 nm absorbance by reaction with Griess reagent (sulfanilamide and naphthalene-ethylene diamine dihydrochloride). Similarly, co-culture with MSCs significantly enhanced NO production in oxLDL treated HUVECs (FIG. 1D). Together, these data suggest oxLDL-induced HUVEC damage can specifically attract MSCs, which protect HUVECs from oxLDL-induced loss in the levels of phospho-Akt, phospho-eNOS, total eNOS, and NO production.

Figure 2A:
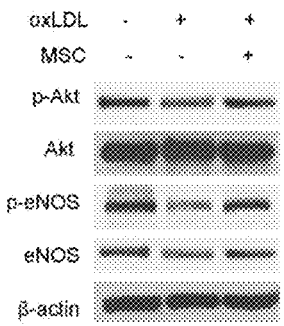
FIGS. 2A-2E show the effect of transplantation of mouse MSCs on high-fat diet-fed apoE$^{-/-}$ mice. The FIG. 2A shows that MMECs ($1.5 \times 10^4$ cells) were treated without or with 50 μg/mL oxLDL in the absence or presence of indirect co-culture with mouse MSCs ($5 \times 10^3$ cells) in each well of 24-well plate for 24 h, followed by cell recovery for Western blot analysis. The FIG. 2B-2D show that the high-fat diet-fed apoE$^{-/-}$ mice treated without (PBS, vehicle control) or with MSCs ($2 \times 10^5$ cells) were sacrificed at 1 week after treatment. The FIG. 2B shows the concentration-response curves of acetylcholine-dependent relaxation (Left panel), sodium nitroprusside-dependent relaxation (Middle panel), and phenylephrine-dependent contraction (Right panel) (n=5-6 in each group). *p<0.05, p<0.01, *p<0.001 MSC vs vehicle control at indicated concentration. The FIG. 2C shows that the aortas subjected to plaque formation analysis by Oil Red O staining were longitudinally incised. The FIG. 2D shows the representative atherosclerotic lesions are red in color (left panel), and the representative aortic root micro sections which show the plaque formation (right panel). The FIG. 2E shows the quantitative data which are expressed as percentages of the total luminal surface area of the aorta (n=3-4 in each group), *p<0.05. The FIG. 2E (left panel) shows the immunostaining of phospho-Akt and phosphor-eNOS protein expression. The representative aortic root sections show phosphor-Akt and phospho-eNOS expression in the endothelial lining (right panel). The quantitative data are expressed as percentages of immunopositive cells of total endothelial lining cells (n=3-4 in each group). *p<0.05. Scale bar=500 μm in FIG. 2D and 50 μm in FIG. 2E (2D=40×, 2E=400× magnification).

Example 2. MSCs Restore Endothelium-Dependent Relaxation and Inhibit Plaque Formation in an Animal Model of Atherosclerosis Because our data showed MSCs specifically homed to and restored the Akt/eNOS activation of oxLDL-treated endothelial cells in vitro, we hypothesized systemic application of exogenous MSCs may repair the atherosclerotic endothelium or ameliorate plaque formation in animal models of atherosclerosis. Before application to the animal study, we confirmed mouse MSCs also restored the levels of Akt/eNOS phosphorylation and total eNOS that were suppressed by oxLDL in mouse endothelial cells, MMECs (FIG. 2A). Mouse brain microvascular endothelial cells (MMECs) were isolated from 4- to 6-week old C57BL/6 mice. The cells were then cultured in DMEM-HG+10% FBS.

Figure 2B:
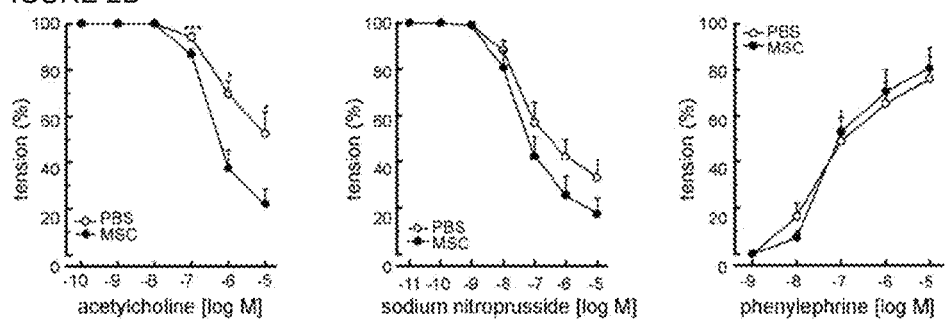

We then investigated whether a single intravenous infusion of MSCs ($2 \times 10^5$ cells) from mice improved endothelial function in Apo-$E^{-/-}$ mice fed a high-fat diet for 5 weeks. At 7 days of MSC treatment, plasma lipid concentrations following high-fat diet feeding were not different between apoE$^{-/-}$ animals treated with PBS (total cholesterol: 405.3±51.9 mg/dL, triglycerides: 58.1±14.1 mg/dL) and MSCs (total cholesterol: 412.2±34.8 mg/dL, triglycerides: 87.4±15.8 mg/dL), suggesting infusion of MSCs does not have effect in the control of plasma lipid concentrations. However, tension recording of aortic rings revealed treatment with MSCs significantly increased the value of acetylcholine-dependent relaxation, but not the values of sodium nitroprusside-dependent relaxation and phenylephrine-dependent contraction, as compared to treatment with PBS (FIG. 2B), suggesting that MSCs improved endothelium-dependent vasodilatation, but not vasodilation dependent on vascular smooth muscle cells or contraction.

Figure 2C:
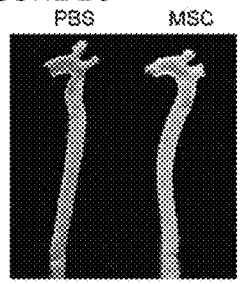
Figure 2D:
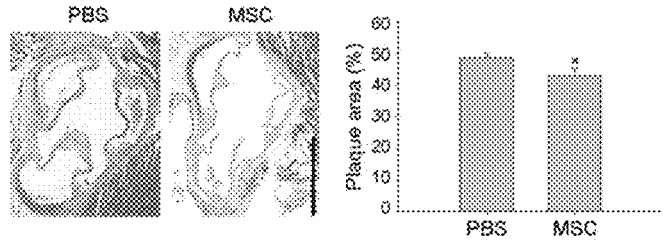

Moreover, we found that tMSCs decreased aortic plaque burden as compared to PBS (FIGS. 2C and 2D). The FIG. 2C shows that the aortas subjected to plaque formation analysis by Oil Red O staining were longitudinally incised. For the quantification of atherosclerotic lesions of apoE$^{-/-}$ mice, serial sections were cut through the aorta at the origins of the aortic valve leaflets, and 40 serial sections from the aortic sinus of each mouse were collected. For endothelial integrity, the aorta was not perfused with normal saline to prevent perfusion-related endothelial injury. Every tenth section (5 µm) throughout the aortic sinus (200 µm) was H&E stained and the photomicrograph was taken. The cross sectional area of a given photomicrograph was analyzed using a computer imaging graphic software (IPWin32). Mean lesion area was quantified from the average of five digitally captured sections per mouse.

In immunohistochemistry study, Mouse sections were deparaffinized in xylene and hydrated in water. Tissue sections were pretreated with 3% $H_2O_2$ for 10 min at room temperature to inactivate the endogenous peroxidase. Sections were blocked in PBS containing 1% BSA and 1% goat serum at 37° C. for 30 min. The sections were incubated with the appropriate Ab overnight, followed by wash with PBS. Slides were then incubated with a secondary Ab (goat anti-rat, BD Pharmingen, San Diego, Calif.) for 30 min. After washing with PBS 3 times, color was developed with 0.1% 3,3'-diaminobenzidine (DAB). A negative control was performed by incubating the sections with secondary Ab only (omission of primary Ab). The sections were then counterstained with hematoxylin and examined by light microscopy. To focus on the signal changes of the endothelial cell, the phospho-Akt and phospho-eNOS positive cells were quantified in the endothelial layer from the sections and averaged.

Figure 2E:
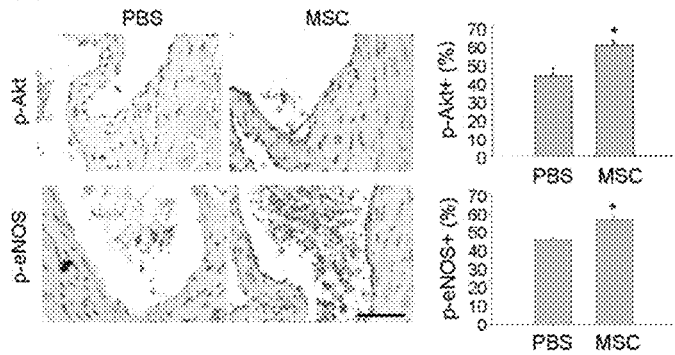

Consistent with the in vitro findings, MSCs also significantly increased the levels of Akt/eNOS phosphorylation in the aortic endothelium, compared to PBS (FIG. 2E). These data suggest exogenous MSCs provide endothelium repair and plaque prevention benefits in an animal model of atherosclerosis.

Figure 3A:
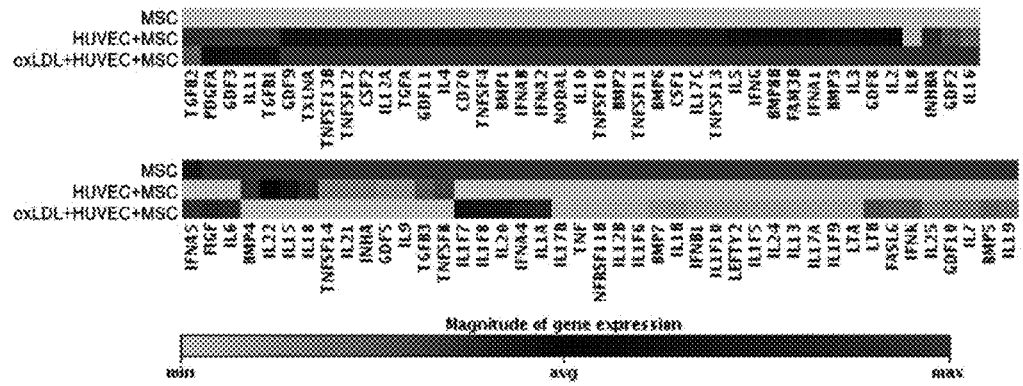
FIGS. 3A-3F shows the IL8 for MSC-mediated effects on oxLDL-induced HUVEC damage. The FIGS. 3A-3B show the aliquots of MSCs ($2 \times 10^4$ cells) alone, or indirect coculture with HUVECs ($6 \times 10^4$ cells) in the absence (HUVEC+MSC) or presence of 50 μg/mL oxLDL for 24 h were assayed for quantitative RT-PCR. The FIG. 3A shows the representative picture of heat map which showing the relative mRNA levels as analyzed by the RT$^2$ Profiler PCR Array. The IL8 gene expression is increased in oxLDL+HUVEC+MSC compared to MSC alone or HUVEC+MSC. The FIG. 3B shows the quantitative RT-PCR for IL8 mRNA levels. The FIG. 3C shows the western blot analysis of HUVECs which treated without or with 50 μg/mL oxLDL for 24 h in the absence or presence of indicated folds of condition medium derived from oxLDL-treated MSCs (CM). The FIG. 3D (lower panel) followed by immunoblotting with anti-ubiquitin Ab of HUVECs treated without or with 50 μg/mL oxLDL for 24 h in the absence or presence of MSCs, IL8, anti-IL8 Ab or PI3K inhibitor LY294002, and FIG. 3D (upper panel) shows the level of p-Akt and p-eNOS. The FIG. 3E shows the immunoprecipitation with anti-eNOS Ab which followed by immunoblotting with anti-ubiquitin Ab of HUVECs treated without or with 50 μg/mL oxLDL for 24 h in the absence or presence of MSCs, IL8, or anti-IL8 Ab. The FIG. 3F shows the influence of MSC or IL8 on eNOS protein stability in the HUVECs. Under the treatment of HUVECs with cycloheximide, down-regulation of eNOS level after exposure to oxLDL is improved after MSC treatment. Treatment with MG132 abolished the down-regulation of eNOS level and the effect is similar to the MSC treatment group. IL8: 10 ng/ml. IL8 Ab: 1500 ng/ml. LY294002: 20 μM.
Figure 3B:
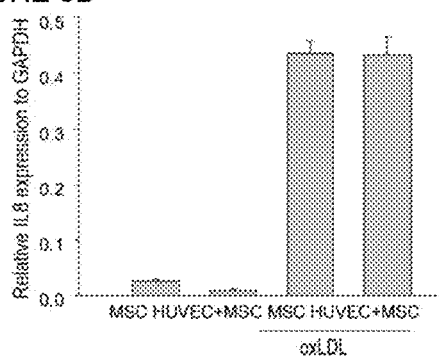

Example 3. IL8 is Required for MSCs-Mediated Restoration of Akt/eNOS Activation and eNOS Stabilization The data from Example 1 and 2 showed that indirect coculture of human MSCs restored the levels of Akt/eNOS activation and total eNOS in oxLDL-treated HUVECs, suggesting a paracrine effect was involved. When analyzing the cytokine and chemokine profiles of MSCs using a human PCR array, we then identified IL8 as the only cytokine or chemokine that MSCs increased in expression upon exposure to oxLDL in the presence of HUVECs (FIG. 3A). A second experiment with quantitative RT-PCR confirmed oxLDL alone, independent of the presence or absence of HUVECs, enhanced IL8 expression by MSCs (FIG. 3B).

The mRNA levels were quantified by real-time RT-PCR array on the $RT^2$ Profiler PCR Array of Human Cytokines & Chemokines Array (SABiosciences, Frederick, Md.) according to the manufacturer's instructions. Briefly, total RNA (2 µg) was reverse-transcribed into first-strand cDNA and used as a template to perform real-time PCR on the ABI PRISM 7700 sequence detection system (Applied Biosystem, Foster City, Calif.). The PCR annealing step was at 60° C. for 30 sec. PCR amplification of glyceraldehyde-3-phosphate dehydrogenase and hypoxanthine guanine phosphoribosyl transferase 1 was performed for each sample to control for sample loading and allow for normalization between samples. The data were analyzed using the comparative ΔΔCt method, according to the PCR Array Data Analysis downloaded from the SABiosciences website. Expression of the target gene SDF-1α, IL8, MIP-2 and the endogenous reference GAPDH was quantified using the primers, probes, and standards. The primers and TaqMan probes were designed using the software Primer Express (Applied Biosystem). RT-PCR was performed according to a TaqMan 2-step method using an ABI PRISM 7700 sequence detection system (Applied Biosystem).

Figure 3C:
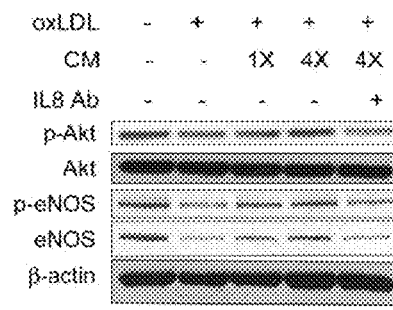
Figure 3D:
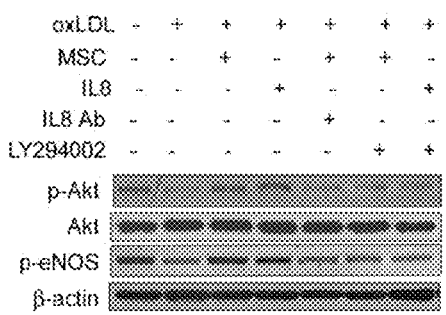
Figure 3D:
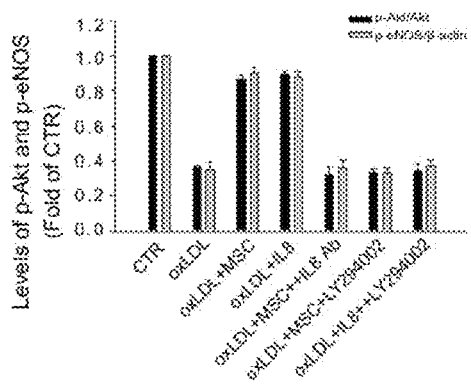

Because the paracrine factors that cells secrete can be accumulated in the condition medium, we used the condition medium derived from oxLDL-treated MSCs (CM-MSC) for the study (FIG. 3C). The CM-MSC reversed the inhibitory effect of oxLDL on the levels of Akt/eNOS phosphorylation and total eNOS in a dose-dependent manner. The beneficial effect of CM-MSC was blocked by adding IL8 neutralization antibodies (Ab) at the same time (FIG. 3C). Moreover, replacement of CM-MSC with IL8 also increased the levels of phosphorylated Akt and eNOS in oxLDL-treated endothelial cells (FIG. 3D). We further demonstrated the involvement of the phosphatidylinositol 3'-kinase (PI3K)/Akt pathway in indirect coculture of MSCs or IL8-mediated effect. The PI3K inhibitor, LY294002, significantly blocked the beneficial effect of MSCs or IL8 on oxLDL-induced changes in Akt and eNOS phosphorylation (FIG. 3D).

Figure 3E:
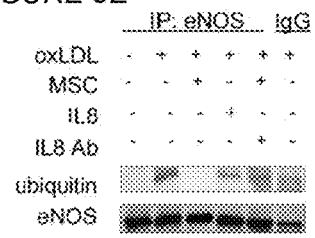
Figure 3F:
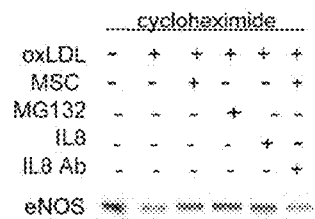

In addition, we also examined whether indirect co-culture of MSCs or treatment with IL8 attenuated the eNOS protein degradation induced by oxLDL. Immunoprecipitation using anti-eNOS Ab following immunoblotting with anti-ubiquitin Ab discovered the ubiquitination of eNOS was markedly attenuated by MSCs (FIG. 3E). The effect of attenuation of eNOS ubiquitination by MSCs could be blocked by IL8 Ab (FIG. 3E). The effect of attenuation of eNOS ubiquitination was also observed in the presence of IL8 alone (FIG. 3E). Moreover, under the treatment of HUVECs with cycloheximide, which blocks protein synthesis, down-regulation of eNOS expression after exposure to oxLDL was noted and improved after MSC treatment (FIG. 3F). Treatment with MG132, the proteasome inhibitor, abolished the down-regulation of eNOS protein level and the effect was similar to the MSC treatment group. Besides, the up-regulation of eNOS by MSCs could be blocked by IL8 Ab. Moreover, IL8 treatment alone also up-regulated eNOS level and the effect was similar to the MSC treatment group. These data suggest, besides the effect of the activation of phosphorylated-eNOS, MSC also attenuates eNOS ubiquitination and IL8 may play a key role in the paracrine effects of MSCs.

Figure 4A:
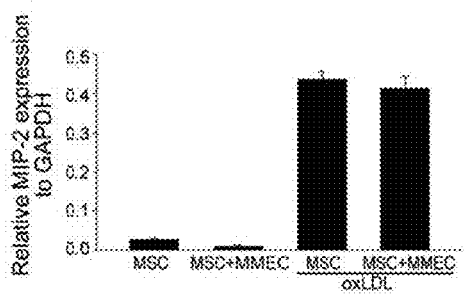
FIGS. 4A-4D shows the MSC-mediated effects on high-fat diet-fed apoE$^{-/-}$ mice depends on MIP-2. The FIG. 4A shows that the mouse MSCs without or with indirect coculture with MMECs in the absence or presence of 50 μg/mL oxLDL for 24 h were assayed for quantitative RT-PCR. The FIGS. 4B-4D shows the high-fat diet-fed apoE$^{-/-}$ mice treated with MSCs ($2 \times 10^5$ cells) that were pretreated with MIP-2 Ab or control isotype IgG were sacrificed at 1 week after treatment. The FIG. 4B shows the concentration-response curves of acetylcholine-dependent relaxation (left panel), sodium nitroprusside-dependent relaxation (middle panel), and phenylephrine-dependent contraction (right panel) (n=5-6 in each group), *p<0.05, p<0.01, *p<0.001 MIP-2 Ab vs control isotype IgG at indicated concentration. The FIG. 4C (left panel) shows the representative aortic root micro sections show the plaque formation, and the quantitative data are expressed as percentages of immunopositive cells of total endothelial lining cells (right panel) (n=3-4 in each group). The FIG. 4D (left panel) shows the immunostaining of phospho-Akt and phosphor-eNOS protein expression. The Representative aortic root sections show phosphor-Akt and phospho-eNOS expression in the endothelial lining. The FIG. 4D (right panel) shows that the quantitative data are expressed as percentages of immunopositive cells of total endothelial lining cells (n=3-4 in each group), *p<0.05. Scale bar=500 μm in C and 50 μm in D (4C=40×, 4D=400× magnification).

Example 4. MIP-2 is Required for MSCs-Mediated Restoration of Endothelium-Dependent Relaxation In this example, the involvement of MIP-2, the IL8 homolog of mice, in MSCs-mediated beneficial effects was elucidated in high-fat diet-fed Apo-$E^{-/-}$ mice. Mouse MSCs were obtained from 4- to 6-week old C57BL/6 mice, and cultured in α-MEM supplemented with 10% FBS. Mouse brain microvascular endothelial cells (MMECs) were isolated from 4- to 6-week old C57BL/6 mice. The cells were then cultured in DMEM-HG+10% FBS. The pattern of MIP-2 expression as analyzed by quantitative RT-PCR in oxLDL-exposed mouse MSCs was similar to IL8 expression in oxLDL-exposed human MSCs (FIG. 4A). To further elucidate the role of MIP-2 in the paracrine effect of MSCs in vivo, MSCs were pretreated with either anti-MIP-2 Ab (clone #40605, IgG2bg, R&D Systems, Minneapolis, Minn.) or control isotype IgG (clone #141945, IgG2b, R&D Systems) before injection into the high-fat diet-fed apoE$^{-/-}$ mice. Moreover, at the end of the 5-week treatment period with high fat diet, apoE$^{-/-}$ mice also received a single-dose of MIP-2 (50 µg/kg) without cell by intraperitoneal injection.

Figure 4B:
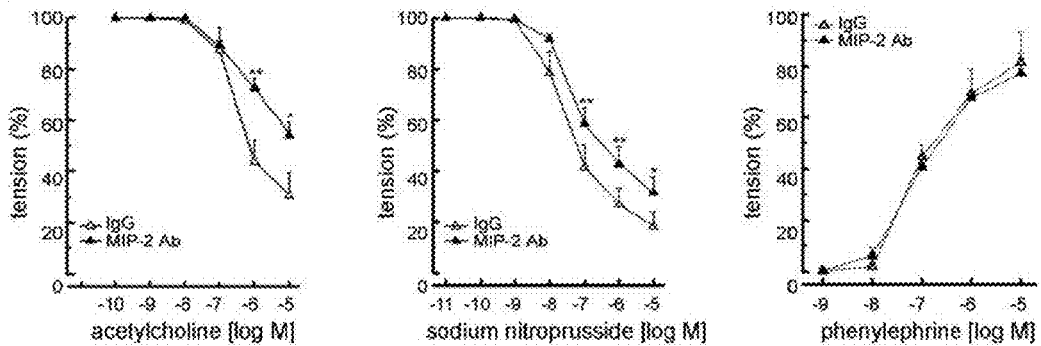
Figure 4C:
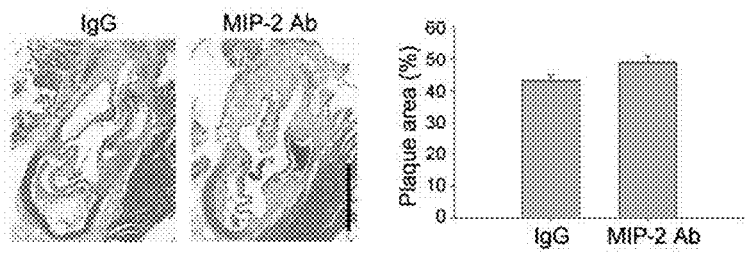
Figure 4D:
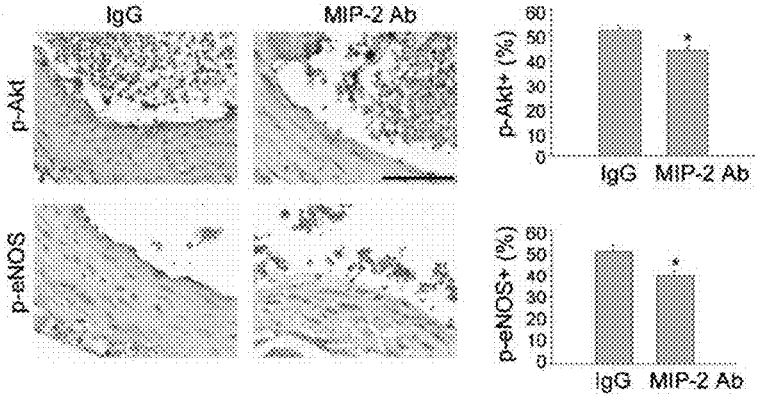

As a result, the improvement in acetylcholine-dependent relaxation of aortic rings at 7 days after infusion with mouse MSCs was significantly blocked by pretreatment of mouse MSCs with anti-MIP-2 Ab but not with isotype IgG (FIG. 4B). A trend to abrogate the beneficial effect of MSCs on aortic plaque burden was also observed after pretreatment of mouse MSCs with anti-MIP-2 Ab compared to isotype IgG, though a significant difference was not achieved (FIG. 4C). Moreover, the MSCs-mediated increase in the percentages of phospho-Akt+ and phospho-eNOS+ endothelial cells were significantly blocked by pretreatment of MSCs with anti-MIP-2 Ab compared to isotype IgG in vivo (FIG. 4D). Together these data suggest systemic application of exogenous MSCs repairs the diseased endothelium and improves endothelial function via secretion of the IL8 homolog, MIP-2, by mouse MSCs.

Example 5. MIP-2 Restores Endothelium-Dependent Relaxation

To demonstrate MIP-2 is essential in mediating the effects of MSCs in protecting endothelium from atherosclerosis-induced dysfunction and inhibiting plaque formation, the direct effect of MIP-2 on restoring endothelial function and inhibiting plaque formation was evaluated in this Example.

Figure 5A:
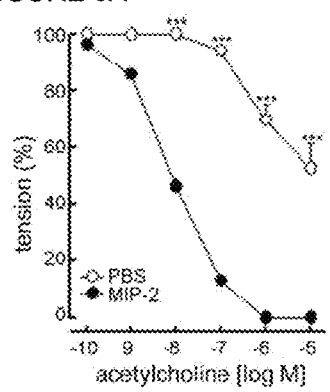
FIGS. 5A-5C show the MIP-2 restored endothelium-dependent relaxation, wherein the high-fat diet-fed apoE$^{-/-}$ mice treated without (PBS, vehicle control) or with MIP-2 (50 μg/kg) were sacrificed at 1 week after treatment. The FIG. 5A shows the concentration-response curves of acetylcholine-dependent relaxation (n=5-6 in each group), *p<0.05, *p<0.01, *p<0.001 MIP-2 vs vehicle control at indicated concentration. The FIG. 5B (left panel) shows that the representative aortic root micro sections show the plaque formation. The FIG. 5B (right panel) shows that the quantitative data are expressed as percentages of the total luminal surface area of the aorta (n=3-4 in each group). The FIG. 5C (left panel) shows the immunostaining of phospho-Akt and phosphor-eNOS protein expression. The representative aortic root sections show phosphor-Akt and phospho-eNOS expression in the endothelial lining. The FIG. 5C (right panel) shows that the quantitative data are expressed as percentages of immunopositive cells of total endothelial lining cells (n=3-4 in each group), *p<0.05. Scale bar=500 μm in B and 50 μm in C (5B=40×, 5C=400× magnification).
Figure 5B:
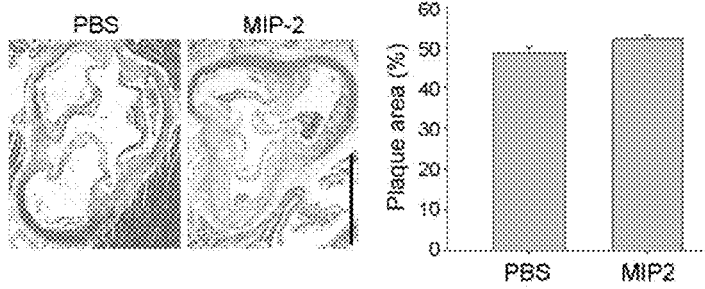
Figure 5C:
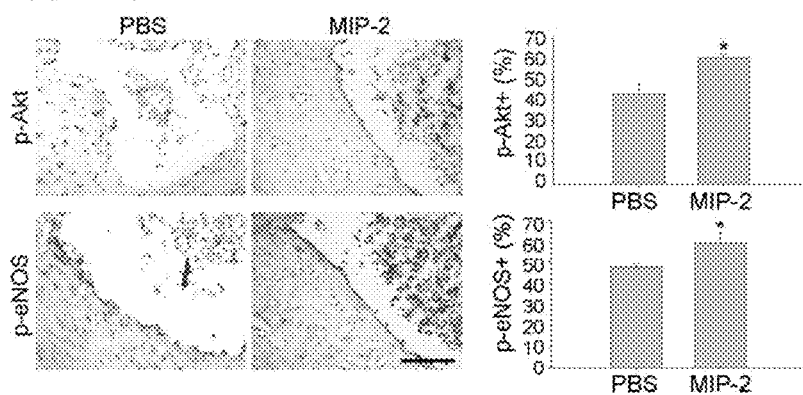

Intraperitoneal injection of high-fat-diet-fed apoE$^{-/-}$ mice with MIP-2 (50 µg/kg) significantly increased the acetylcholine-dependent relaxation of aortic rings at 7 days compared to vehicle alone (FIG. 5A). The therapeutic potential of MIP-2 on improving the endothelial function is obvious, even with a single dose injection. However, the effect of a single-dose MIP-2 on aortic plaque burden was not different from that of vehicle alone (FIG. 5B). Moreover, similar to the effects of MSCs, we also found MIP-2 significantly increased the percentages of phospho-Akt+ and phospho-eNOS+ aortic endothelium in high-fat diet-fed Apo-E$^{-/-}$ mice compared to treatment with the vehicle alone (FIG. 5C). These data together suggest MIP-2 is involved in MSCs-mediated effects in restoring the endothelial function.

Example 6. Cell Trafficking of MSCs

To explore whether MSCs mediate repair of atherosclerotic endothelium via engraftment, MSCs were labeled with CFSE before i.v. infusion. The high-fat diet-fed apoE$^{-/-}$ mice treated without (PBS, vehicle control) or with CFSE-labeled MSCs ($2 \times 10^5$ cells) were sacrificed at 1 week after treatment and aortic rings were recovered for immunohistochemistry study using anti-CFSE Ab. Aortic rings of mice infused with or without CFSE-labeled MSCs were recovered for the detection of MSC engraftment.

Figure 6:
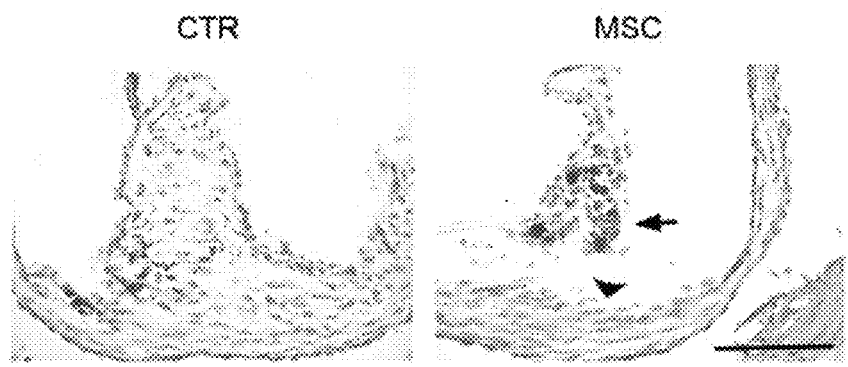
FIG. 6 shows the In vivo trafficking of transplanted mouse MSC. The high-fat diet-fed apoE$^{-/-}$ mice treated without (PBS, vehicle control) or with CFSE-labeled MSCs ($2 \times 10^5$ cells) were sacrificed at 1 week after treatment and aortic rings were recovered for immunohistochemistry study using anti-CFSE Ab. The representative pictures show CFSE-labeled MSCs (arrow) that are distant from the endothelial lining (arrowhead). Scale bar=100 μm. (200× magnification).

As showed in FIG. 6, CFSE-labeled MSCs could be detected at 7 days at areas close to but not actually inside the endothelium, while no cells were stained with anti-CFSE Ab in those not treated with MSCs, suggesting a paracrine effect, rather than differentiation, contributed to the therapeutics in atherosclerosis.

Example 7. The p38 Signaling Pathway Involved in the Secretion of IL8

Figure 7A:
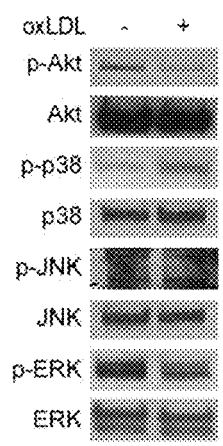
FIGS. 7A-7C show the expression and secretion of IL8 by MSCs depends on oxLDL-activated p38MAPK. The FIG. 7A (western blot analysis) shows the effect of oxLDL on the activated mitogen-activated protein kinases (MAPK) pathways. The level of phosphorylated p38 was increased in MSCs upon exposure to 50 μg/mL oxLDL, while other signaling pathways were not activated. The FIGS. 7B and 7C show the p38 knockdown with transient transfection of shRNA against p38 in MSCs inhibited IL8 expression (FIG. 7B) and secretion (FIG. 7C) as assayed by western blotting (FIG. 7B, upper panel), quantitative RT-PCR (FIG. 7B, lower panel), and ELISA (FIG. 7C).
Figure 7B:
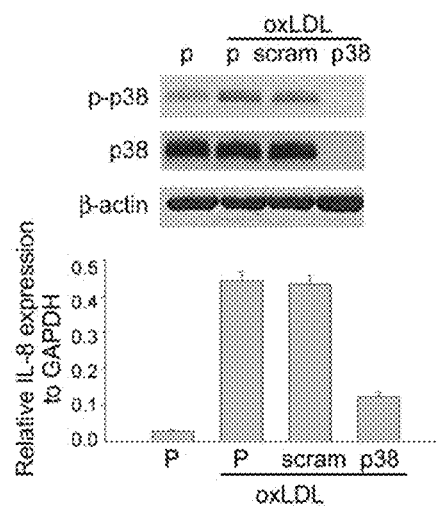
Figure 7C:
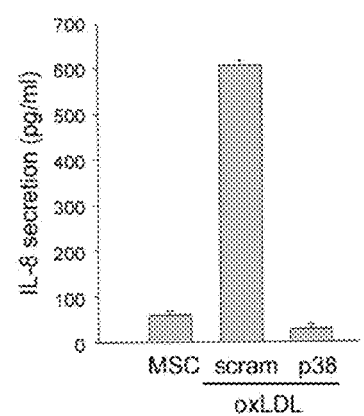

We further elucidated the MAPK signaling pathway involved in the secretion of IL8 by human MSCs. First, it is demonstrated that the level of phosphorylated p38 was increased in MSCs upon exposure to 50 µg/mL oxLDL, while other signaling pathways were not activated (FIG. 7A). Moreover, p38 knockdown with transient transfection of shRNA against p38 in MSCs also inhibited IL8 expression and secretion when exposed to oxLDL (FIG. 7B, C). Together these data suggest the p38/IL8 signaling pathway is involved in the full mechanism of MSC-mediated beneficial effects on endothelial cells.

In conclusion, co-culture with human MSCs reversed the effects of oxLDL on endothelial cells and restored Akt/eNOS activity, eNOS level, and NO production. MSC transplantation improved endothelial function and plaque formation in high-fat diet-fed apoE$^{-/-}$ mice. In the in vitro and in vivo studies, MSCs exert their protective effect on oxLDL-treated endothelial cell through the paracrine effect by secreting IL8/MIP-2. Activation of the Akt/eNOS pathway in endothelium by IL8/MIP-2 is involved in the protective effect of MSCs. The present invention also reveals that the PI3K inhibitor LY294002 significantly blocked the beneficial effect of hMSCs, CM-hMSC, or IL8 on ox-LDL induced inactivation of the Akt/eNOS pathway, and the effect was similar to that of IL8 Ab. It seems that both the p38 and PI3K/Akt signaling pathways are involved in the mechanism of hMSC-mediated beneficial effects on oxLDL-treated endothelial dysfunction.

The present invention identifies the effect of MSCs in the early stage of atherosclerosis for earlier prevention of the development and/or progression of disease. The experimental data described in above Examples suggest that MSCs promote endothelial function through releasing a repertoire of paracrine factors via activation of p38MAPK, and the MSCs or their secretome IL8/MIP-2 may be applied to treat atherosclerotic lesion (atherosclerosis) in patients. They are helpful in the development of protocols for preclinical or clinical trials in the application of MSCs for atherosclerosis treatment.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

The invention claimed is:

1. A method for treating an atherosclerotic lesion, comprising administering a subject in need thereof a therapeutically effective amount of a composition comprising hypoxia-cultured mesenchymal stem cells (MSCs) secreting cytokine IL8 to restore the endothelial function, wherein the atherosclerotic lesion is selected from a group consisting of coronary atherosclerosis, cerebral atherosclerosis, aortic atherosclerosis, and renal artery atherosclerosis.

2. The method of claim 1, which comprises administering a subject in need thereof a therapeutically effective amount of a composition comprising hypoxia-cultured MSCs obtained by culturing allo-MSCs under low oxygen conditions less than 10% oxygen.

3. The method of claim 1, wherein the atherosclerotic lesion is associated with coronary artery disease, stroke, aortic aneurysm, or peripheral arterial disease.

4. The method of claim 1, wherein the composition comprising hypoxia-cultured MSCs is administered through intravenous injection, intracoronary injection, intraperitoneal injection, or local application.

5. The method of claim 4, wherein the composition comprising hypoxia-cultured MSCs is administered once or more in a therapeutic regimen.

6. The method of claim 1, wherein levels of phospho-Akt, phospho-endothelial nitric oxide synthase (eNOS) and total eNOS, and nitrogen oxide (NO) production in the subject are increased through the administration of the composition comprising hypoxia-cultured MSCs.

7. The method of claim 1, wherein a restoration of endothelium-dependent relaxation and an inhibition of plaque formation in the subject are increased through the administration of the composition comprising hypoxia-cultured MSCs.

8. The method of claim 1, wherein the hypoxia-cultured MSCs are obtained by culturing allo-MSCs under a low oxygen condition ranging from 1% to 7% oxygen.

9. The method of claim 8, wherein the hypoxia-cultured MSCs are obtained by culturing allo-MSCs in a gas mixture composed of 94% $N_2$, 5% $CO_2$ and 1% $O_2$.

10. The method of claim 8, wherein the hypoxia-cultured MSCs are obtained by culturing allo-MSCs under a low oxygen condition ranging from 1% to 7% oxygen.

11. The method of claim 1, wherein the MSCs are derived from a bone marrow tissue, adipose tissue, umbilical cord tissue or umbilical cord blood.

12. The method of claim 1, wherein the MSCs are bone marrow MSCs.

13. The method of claim 11, wherein the MSCs are bone marrow MSCs.

\* \* \* \* \*